United States Patent [19]
Benaron

[11] Patent Number: 5,413,098
[45] Date of Patent: May 9, 1995

[54] PATH CONSTRAINED SPECTROPHOTOMETER AND METHOD FOR DETERMINATION OF SPATIAL DISTRIBUTION OF LIGHT OR OTHER RADIATION SCATTERING AND ABSORBING SUBSTANCES IN A RADIATION SCATTERING MEDIUM

[75] Inventor: David A. Benaron, San Mateo County, Calif.

[73] Assignee: Sextant Medical Corporation, Berkeley, Calif.

[21] Appl. No.: 994,947

[22] Filed: Dec. 22, 1992

Related U.S. Application Data

[63] Continuation-in-part of Ser. No. 813,958, Dec. 24, 1991.

[51] Int. Cl.[6] ............................................. A61B 5/00
[52] U.S. Cl. ................................... 128/633; 128/665; 250/332; 250/339.01; 250/343; 356/432
[58] Field of Search ........................ 128/633, 664, 665; 250/332, 343, 339; 356/39, 40, 41, 432; 378/87

[56] References Cited

U.S. PATENT DOCUMENTS

| | | | |
|---|---|---|---|
| 4,515,165 | 5/1985 | Carroll | 128/664 |
| 4,592,361 | 6/1986 | Parker et al. | 128/633 |
| 5,095,207 | 3/1992 | Tong | 250/306 |
| 5,137,355 | 8/1992 | Barbour et al. | 128/664 |
| 5,139,025 | 8/1992 | Lewis et al. | 128/665 |

*Primary Examiner*—Krista M. Pfaffle
*Attorney, Agent, or Firm*—Flehr, Hohbach, Test, Albritton & Herbert; Zimmer, Kevin J.

[57] ABSTRACT

A spectrophotometer for providing an image of a radiation scattering medium having one or more radiation attenuating constituents is disclosed herein. The spectrophotometer includes a light source for illuminating the scattering medium with electromagnetic radiation of at least one wavelength. In one embodiment a time-gated detector serves to detect, during a predefined detection interval, the electromagnetic radiation having traversed a distribution of path lengths during propagation through a region of the medium. A photon counting apparatus or the like measures the intensity of the detected portion of the electromagnetic radiation, wherein the measured intensity is a function of attenuation of the region within the medium. A display apparatus is operative to generate the image in accordance with the measured intensity.

38 Claims, 11 Drawing Sheets

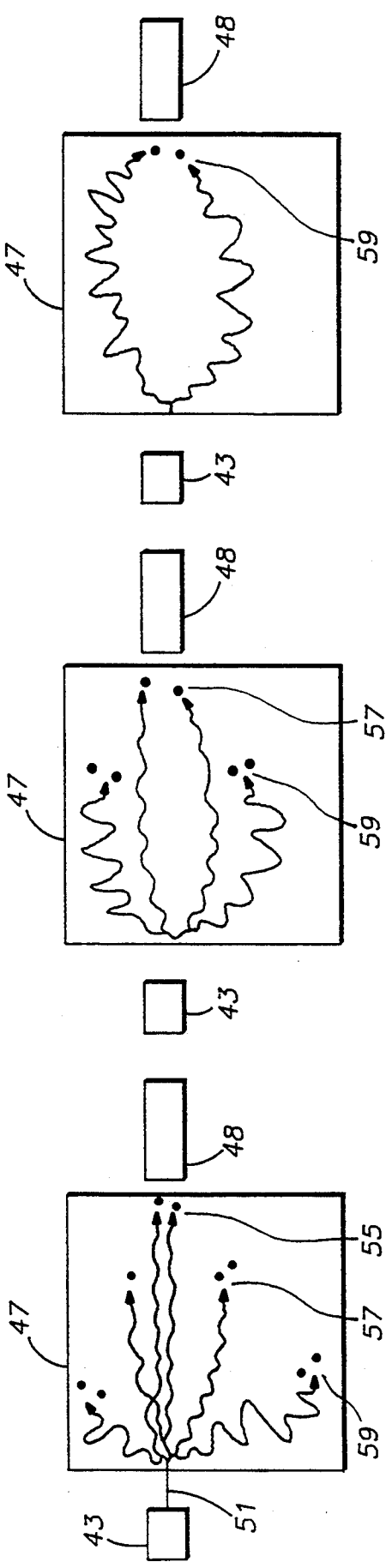
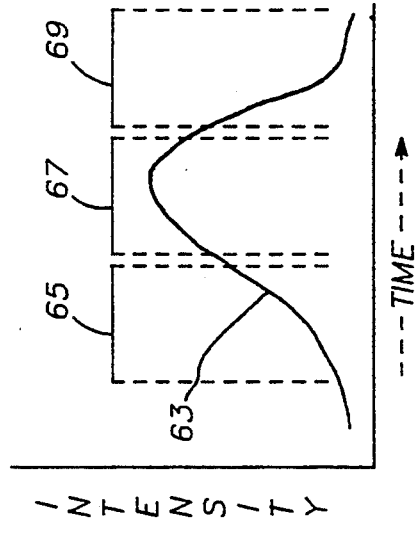
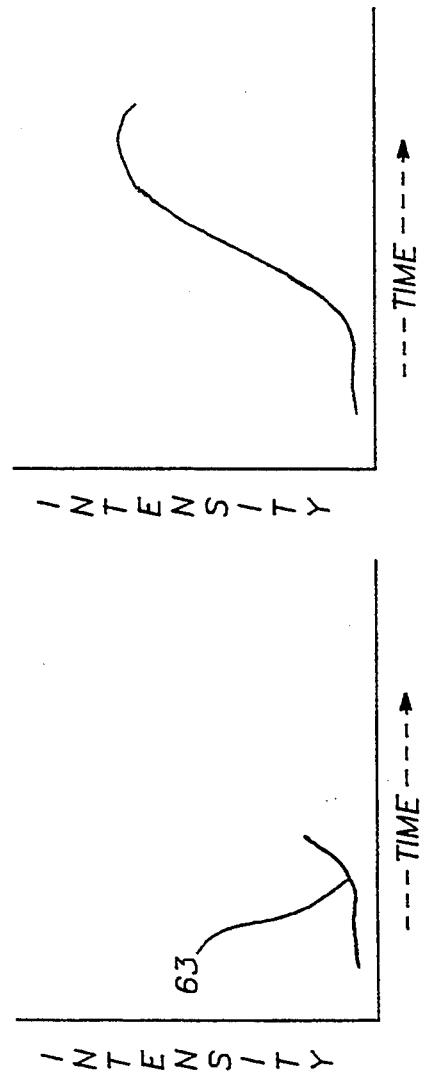

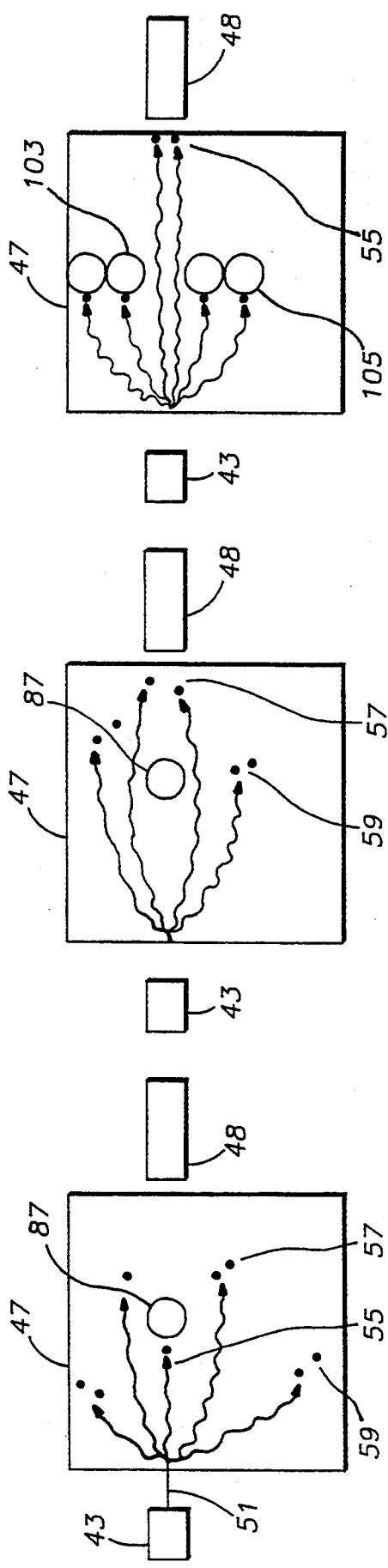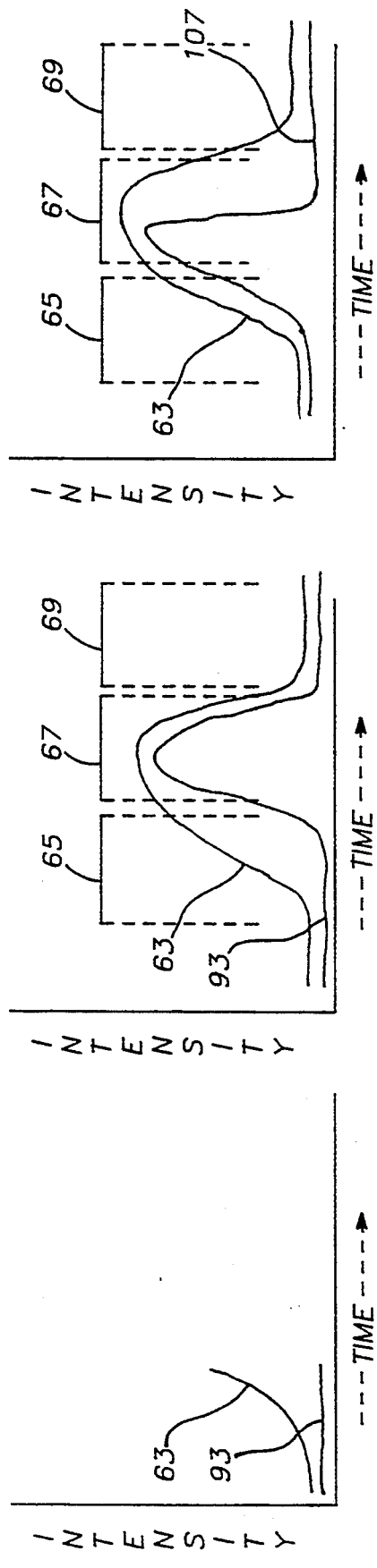

PATH CONSTRAINED SPECTROPHOTOMETER AND METHOD FOR DETERMINATION OF SPATIAL DISTRIBUTION OF LIGHT OR OTHER RADIATION SCATTERING AND ABSORBING SUBSTANCES IN A RADIATION SCATTERING MEDIUM

This application is a continuation in part of copending U.S. patent application Ser. No. 07/813,958, filed on Dec. 24, 1991.

FIELD OF THE INVENTION

This invention relates to a quantitative imaging device and method, and more particularly relates to a non-invasive spectrophotometer and method for measuring the absorbance of light or other radiation as it passes through a medium, wherein the measured light or radiation is detected subsequent to propagation through the medium for a predefined period of time. In this way only light traversing a narrowly defined range of path lengths through the medium is detected, whereby the spatial distribution of the concentration of light absorbing or other radiation absorbing substances, such as materials in luggage presented at airport checkpoints, or the location of tumors in breast tissue, or the concentration of hemoglobin in living human tissues, and others, can be quantitatively assessed in a spatial manner, and imaged in a useful fashion.

RELEVANT LITERATURE

A list of references cited herein is provided to assist in the study of this application, as follows:

| U.S. Pat. Nos. CITED | | | |
|---|---|---|---|
| 4,305,398 | 12/1981 | Sawa | 128/633 |
| 4,805,623 | 2/1989 | Jöbsis | 128/633 |
| 4,819,752 | 4/1989 | Zelin | 128/633 |
| 4,859,057 | 8/1989 | Taylor et at. | 356/41 |
| 4,972,331 | 12/1990 | Chance | 364/550 |
| 07/499,084 | pending | Benaron | 356 |
| 07/612,808 | pending | Benaron | 356 |

OTHER PUBLICATIONS

Benaron, D. A., et al. (1991). "Optical path length of 754 nm and 816 nm light emitted into the head of infants." Proceedings of the IEEE Engineering in Medicine and Biology Society 1990:3:1117-9.

Benaron, D. A. (1992). "2-D and 3-D Images of Thick Tissue Using Time-Constrained Time-of-Flight (tc-TOFA) Spectrophotometry." Submitted to Proceedings of the International Society for Optical Engineering for presentation in January 1992.

Schlereth F., et al. "Imaging in diffusing media: a problem in large-scale computing." Submitted to Proceedings of the International Society for Optical Engineering for presentation in January 1992, Text not yet available.

Shy K. K. et at. "Effects of electronic fetal-heart-rate monitoring, as compared with periodic auscultation, on the neurologic development of premature infants," New England Journal of Medicine, March 1990, p588-93.

BACKGROUND OF THE INVENTION

Determining the distribution of light absorbing substances which are located inside an opaque, light-scattering medium that hides the substances from view can be difficult. For example, forming an image of objects inside luggage presented at an airport checkpoint can require the use of x-rays, which may be harmful to those nearby, fog photographic film, and fail to detect certain plastic weaponry or explosives. Similarly, the detection of tumors inside the human body is difficult, and limited by the need to use x-rays or cumbersome magnetic imaging techniques, by the inability to image some types of tumors, and by cost. Lastly, identification of the amount of oxygen in blood deep inside the human body is of central importance in the medical management of many patients. For example, adults suffering heart attacks, children with severe asthma, and prematurely born babies, all need close monitoring of the amount of oxygen in their blood, and this can be determined in superficial tissues using photodetectors, but this method does not yield spatial information, leaving deep tissues, such as the heart itself or the fetus in the womb beyond the range of measurement. Currently available methods to image substances deep inside a light scattering body are hampered by physical limitations inherent in those methods. For example, the use of x-rays carries health risks, and does not image all substances. The use of sound waves, such as ultrasound, is limited by an inability to measure through air/fluid interfaces, and the images are not clear. Magnetic Resonance Imaging (MRI) is limited by the need for large, expensive, magnetically-shielded facilities, and is not appropriate for many situations.

Several techniques exist in the art which use light to measure substances in a scattering medium, but all contain significant drawbacks that prevent or hamper their usage as spatial imaging modalities. For example, reflectance pulse oximetry, taught by Taylor et al. (U.S. Pat. No. 4,859,057) and Sawa (U.S. Pat. No. 4,305,398), uses light reflected back from the skin or eye to measure the saturation of blood with oxygen. However, these measurements are only skin deep. Reflection oximetry does not reveal the distribution in space of this blood, only information about blood in the superficial tissues. Internal organs remain out of range because pulse oximetry devices do not work well when their light is directed deep into a body, for reasons due to the physics of the measurement, to be outlined below. Thus, despite recent improvements, there is currently no easy way to measure, for example, the quantity of oxygen a fetus is receiving while in its mother's womb. This lack of an adequate method to test fetal saturation contributes to unnecessary emergency surgical deliveries (Shy et. al., 1990), as well produces babies with cerebral palsy who went without adequate oxygen, but in whom this low oxygen level was not detected due to the lack of a simple, non-invasive method of checking fetal oxygen. Another example of the need for improvement in measurement is with newborns babies, who often undergo painful blood tests because there is no in vivo method at this time that quantitatively measures jaundice, an excess of light absorbing substance called bilirubin. A final example is the adult who needs x-rays to determine if a bone is broken, whereby the lack of a simple optical method necessitates the use of x-irradiation.

The limitations in current methods of optical spectroscopy, such as pulse oximetry and other methods of spectroscopy, are due to physical laws governing the measurements themselves, and these inherent limitations will become self evident upon close study of the mathematical relationship called Beer's Law, $$A = \epsilon CL, \tag{1}$$

where absorbance of light (A) equals a known constant ($\epsilon$) times the concentration of measured substance (C) times the path length of light through the tissue (L). The foundation for nearly all optical spectrophotometry, and of much of the spectrophotometry using other types of radiation in the art, whether specified outright or empirically derived, is Beer's Law rearranged to solve for concentration, as:

$$C = A/\epsilon L. \tag{2}$$

One problem encountered in implementing Beer's Law is that the path taken by photons of light as they travel through a light scattering medium is different for each photon. The same is true for other types of radiation, but light alone will be considered here for simplicity. Some photons travel straight through the medium, thus taking the shortest possible path, while others meander through the medium, thus taking a much longer path and taking much longer to pass through the medium. As a whole, the paths taken by a single large group of photons passing through the medium at the same time are multiple, and the paths are tortuous and irregular, so that a single exact path length L does not exist. Thus, when attempts to solve Beer's Law are made, there is no true L value that can be used. The fact that light has scattered prevents solution to Beer's Law, in all but specialized cases. In fact, Benaron (1991) was the first to show that even the range of path length L was so variable, even for common tissues such as brain, that path lengths must be measured in order to achieve an accurate estimate of absorption.

Jöbsis (U.S. Pat. No. 4,805,623) was the first to attempt to address this problem. His device estimates a path length in a tissue with a known thickness and concentration of light absorbing substance, and then using the relative absorbance of that reference compared to a tissue under study, attempts to correct for uncertainties in path length. There are five major limitations inherent in Jöbsis' approach, outlined in Benaron (pending U.S. Pat. No. 07/612,808). Chance (U.S. Pat. No. 4,972,331) introduces a modulated light source in order to determine a median time of travel, but this still does not yield spatial information, as the effect of the individual path lengths are blurred by an averaging process. The net result of this averaging process is that, at best, only a median time of travel may be deduced. Further, the intensity of the returning light is not contemporaneously measured, thus precluding the performance of certain analyses.

Benaron (pending U.S. Pat. No. 07/499,084) was the first to introduce true spatial resolution, teaching a pulsed light source that allows identification of a feature of the differing path lengths. When the continuous light used by others is turned off, and a pulsed, non-continuous light source is substituted, all photons entering the medium enter at approximately the same time. As the light source becomes dark after the pulse is produced, timing the exit of photons from the substances gives a clue as to the paths they have traveled. Light that travels the shortest distance through the medium now exits first and can be detected early, whereas light that travels the longest distance through the medium exits last and is detected later. In his patents pending, Benaron teaches how to measure a feature of the detected light signal (such as the brightest time point), which provided some of the information needed to correct Beer's Law for path length. For example, measuring the brightest point, allowed for a calculation of the modal path traveled by photons returning at that point in time. As the speed of light in tissues is relatively constant, all photons returning at that particular time have traveled about the same distance, assuming that they all were emitted at the same moment. This allowed determination of absorbance at one particular path length, but discards the range and other features of the distribution of paths taken.

Benaron substantially improved the power of his initial pulsed, noncontinuous light approach by analyzing the full spectrum of path lengths traveled (U.S. Pat. No. 07/612,808). Using a mathematical deconvolution algorithm, different characteristics of the medium and of the absorbing and scattering substances may be determined using TOFA (time of flight and absorbance) data from one or more points. This allowed determination of a multi-dimensional saturation image yielding absorbance at different depths in the tissue, or even three-dimensional absorbance distribution images. While the approach is effective, Singer et al., (1990) and Schlereth showed that production of an image required significant computer processing.

What is currently needed, and not available in the art, is a device capable of rapidly imaging a function of the absorbance and scattering of light traveling through light scattering tissues, one which does not require massive processing in order to produce an image, that will give real-time image information, and avoid the problems associated with computation-intensive path-length calculations.

SUMMARY OF THE INVENTION

The present invention relates to a time-constrained spectrophotometer that non-invasively and quantitatively determines the spatial concentration of light-absorbing or other radiation absorbing substances in a medium by assessing, at one or more wavelengths, the number of photons transmitted through the medium during a narrow window of time, such that all photons arriving in that particular window have traveled through the medium for approximately the same period of time. As all photons arriving during the narrow window have all traveled the same distance, L becomes a constant, allowing for a quantitative solution to Beer's Law, or derivations of Beer's Law allowing for the effect of scattering of light through tissue, at one point or in many dimensions. Under microprocessor control, a plurality of pulsed light sources are illuminated in sequence. Light returning to one or more photodetectors after passing through said tissue is measured for intensity during the window, which is related to the absorbance and scattering of the light or other radiation by the tissue at different points in time and/or space. The region in space illuminated by the radiation may be carefully controlled by regulating the study window of time-constraint. Results are found by solving multiple equations for multiple unknowns and resolving the data comparing changes over time or across wavelengths to extracting spatial information under microprocessor control, and are output in terms of images in one or more dimensions.

OBJECTS AND ADVANTAGES

The instant invention has many significant inherent advantages over the prior art. First, the spectrophotometer of the invention allows solution of Beer's Law, or solution of more sophisticated equations taking scattering into account, by constraining measured photons to have traveled for a narrowly defined interval of time, thus controlling variance in path length. Once path length L has been made a constant, rather than a distribution of path lengths, Beer's Law can be rapidly solved, such that the distribution of one or more measured substances can be found quantitatively over a short period of time. For example, pulsed light normally returns with a wide variety of traveled paths. If the window is constrained such that only the first photons arriving at the detector are measured, then these photons have all traveled approximately the same distance. Furthermore, these photons could not have undergone scattering, as this would delay the photons, and they would have arrived later, missing the window. The window therefore excludes photons that took a roundabout path the arrive at the detector, because these photons too would be excluded from the early window. Thus, the time-constraint has simplified the analysis greatly, as the only photons measured are those that have traveled a similar path length, for example, those photons that have traveled with minimal scattering between the emitter and detector. The intensity of this minimally scattered light is a function of both the scattering and the absorbance of the light directly in the path between the emitter and detector, but not of the tissues surrounding this straight line. Measurement using a variety of emitter and detector locations produces information which can be analyzed in a standard 2-D grid, or subject to computer reconstruction to produce tomographic images representing 3-D structure. Using such a technique, Applicant has rapidly and successfully imaged diffusive objects suspended in highly scattering media, such as blood admixed with yeast, and has obtained images in vivo of the interior of bodies. In addition, objects not detectable with conventional technology, such as weapons made of plastic hidden in suitcases, can be seen. This represents a major advance of the current art.

A second advantage of this method is that as path length is controlled, the tc-TOFA (or Time-Constrained Time Of Flight and Absorbance) device is not limited to testing locations in which the distribution of path lengths through the medium is constant. Thus, deep substance measurements, such as the interior of luggage or the fetus in the womb, may be measured. Furthermore, displaying the number of photons arriving at each location yields, with a minimum of calculation, an image of the distribution of absorbance and/or scattering in real-time. For example, displaying in a grid the total number of photons in the early time-constrained window example discussed in the above paragraph, yields a picture directly, without detailed calculations. This is important in real-time imaging applications such as luggage screening or for visualization of the interior of living bodies, where lengthy calculations would prevent the use of this method.

Next, the imaging system uses only light, rather than x-rays or ultrasound, and thus may be safer than conventional systems.

It is a further object of this invention to be able to generate and interpret data from multiple wavelengths of light, compensating for these additional variables if needed. Ideally, for simple measurements, such as the interior of luggage, the measurement of light over a constrained path is sufficient to produce a single image of the distribution of multiple substances, though the image would be merely qualitative. In practice, however, there are multiple different substances intervening (e.g., in the human body there are bilirubin, hemoglobin, cytochromes, melanin, etc.). While a derivation of equations dealing with scattering and absorbance by multiple substances is beyond the scope of this discussion, analysis suggests that three or more wavelengths are needed to solve quantitatively for a simple variable such as hemoglobin oxygen saturation, taken simultaneously or in rapid succession. Furthermore, gating of the measurement to heart tones or EKG readings, would allow separation of an arterial and a venous phase, allowing calculation of arterial saturation, similar to the manner used in pulse oximetry, only in a spatial sense. In fact, as the amount of light absorbed by each substance in the medium is related to the true color of the substance, images could be generated that re-create the color of the substance as it appears to our eyes, were we able to remove the substance and look at it. This could be used to make an imaging device in which the liver is brown, bile is green, and tumors would stand out in their true colors.

Further objects are that any technology used is affordable and available, that the device is portable, allowing measurement at a patient's bedside, and that the device gives continuous real time answers, allowing results to be used in medical management. In addition, the provision of a display to allow a user to see results of calculations or images of concentration or saturation, and an alarm device to allow alerting a user when specified values are exceeded, are also objects of the invention.

A salient feature of the present invention is the observation that radiation of certain wavelengths, while both being scattered and absorbed by tissue, can be made to penetrate various types of scattering media. Examples of such scattering media include human tissue, the atmosphere, or even suitcases conventionally inspected by airport scanners. The radiation can then be detected upon reemergence from that material in order to allow formation of images and/or quantitation of the concentration of substances in the interior of the scattering media. The two approaches would ideally be combined in order to yield an image related to concentration distribution.

Another object of the present invention is that this data can be enhanced by collection over time. In many medical applications, the value of a measurement is enhanced by determination of temporal characteristics. For example, in the well-known technique of pulse oximetry, the temporal variance of the absorption of light by arterial blood allows a crude estimation of oxygenation, and this requires resolution of absorbance many times a second. Applying path-corrected approaches to this method should refine the accuracy of the method. Furthermore, the technique can be used to measure venous oxygenation, which may be medically more important as it indicates whether oxygen is present in sufficient amounts to supply the needs of metabolically active tissues, or whether a particular tissue is even able to use oxygen at all (e.g., damaged tissue from stroke or heart attack).

Another object is that oxygen-sensitive proteins can be quantitatively or qualitatively monitored in the body more accurately. These proteins include: hemoglobin, myoglobin, mitochondrial cytochrome aa3, cytosolic cytochrome oxidase, and other copper- or iron-containing proteins. Previous approaches have not measured the path of light through the body, and thus have not been able to quantitate concentration accurately. By combining a path-sensitive measurement with absorbance, a more powerful monitoring technique is generated, containing many of the advantages of earlier techniques in addition to improved accuracy.

In accordance with the invention an improved spectrophotometer measures the intensity of transmitted light from temporally modulated light sources, either a pulsed non-continuous light source or a modulated light source, of multiple discrete or continuous wavelengths in which the time of measurement is constrained to a narrow window, thus simplifying the data analysis. The invention has the unique ability to measure the concentration of a light absorbing or other radiation absorbing substance in a spatial sense, and to provide an image of that distribution. This technique has the advantage of being able to be applied to bilirubin, hemoglobin, and many other light absorbing substances within the human body (whether in skin, blood, internal organs, or even in organs of a fetus within its mother's womb) and in inanimate objects as well. Detection of plastic weaponry in airport checkpoints would be invaluable if loss of life could be prevented. In medicine, the device would provide life saving and treatment guiding data to medical personnel, yet would require relatively little training or skill to operate and would be relatively affordable and portable. Potential uses of the invention are many, and include measurement of brain oxygen saturation in patients with head injuries, safe monitoring of fetuses inside their mother's wombs, and monitoring of central nervous system oxygenation during surgery.

These and other advantages of the invention will become apparent when viewed in light of accompanying drawings and detailed description.

BRIEF DESCRIPTION OF THE DRAWINGS

FIG. 5 illustrates the time of flight principle applied to photons;

FIG. 6 illustrates the effect of objects in or near the path between emitter and detector;

DESCRIPTION OF A PREFERRED EMBODIMENT

Figure 1:
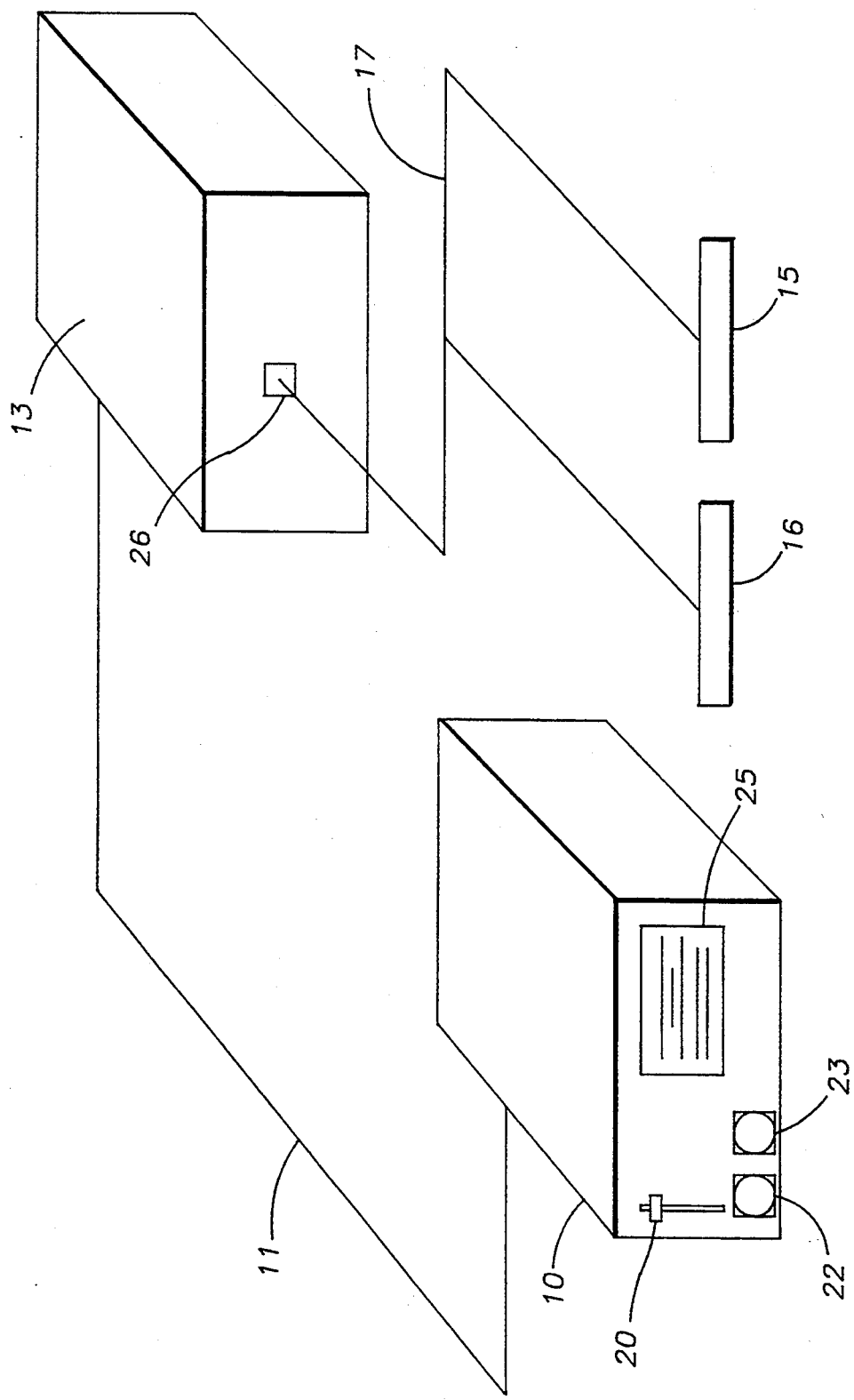
FIG. 1 is a perspective view of a preferred embodiment.

Referring to FIG. 1, this embodiment consists of control unit 10, connected by cable 11 to remote processor 13, in turn connected to sensor source 15 and sensor detector 16 by cable 17. Power is controlled by switch 20 and adjustment of the device is provided by controls 22 and 23. A display panel 25, consisting of one of more lines of readout or an image of the distribution of absorbance is on control unit 10. In addition, cable 17 connects to remote processor 13 by way of detachable plug 26, to allow different probes 15, detectors 16, and cables 17 to be used with the same control unit 10 and remote processor 13 pair.

Figure 2:
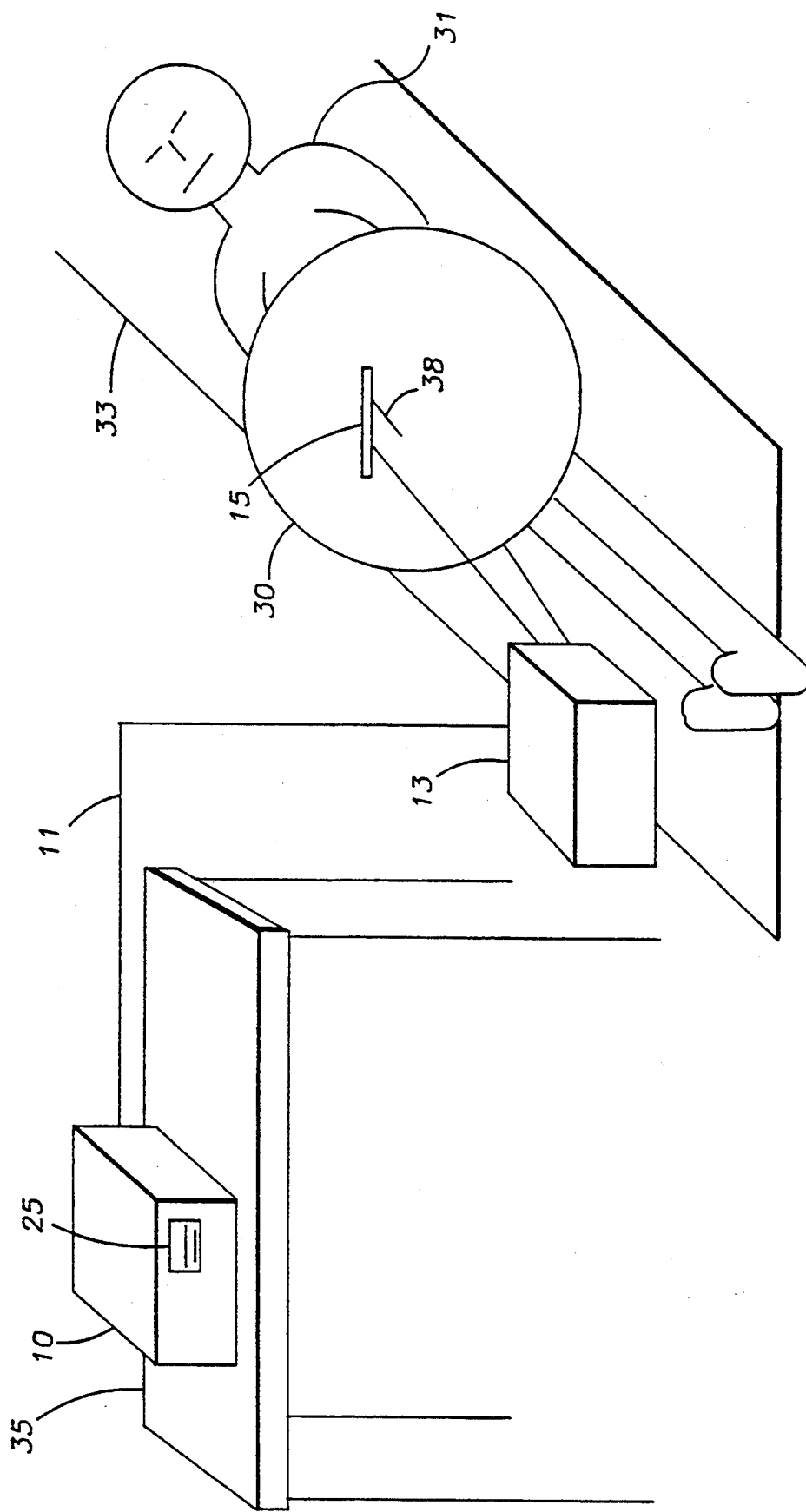
FIG. 2 is a schematic view of the spectrophotometer attached to a patient.

Referring now to FIG. 2, sensor source 15 is shown attached to an abdomen 30 of patient 31 in labor. Detector 16, hidden from view, is under the patient. Remote processor 13 is situated on labor bed 33 to minimize interference with initial processing, while control unit 10 is placed on separate table 35 with display 25 within clear view of those in labor room. Control on abdomen 30 and measures oxygen saturation of a fetus inside (not shown), though alternatively, probe 15 could be applied through a cervix and attached to a fetus' head by use of suction port 38.

Figure 3:
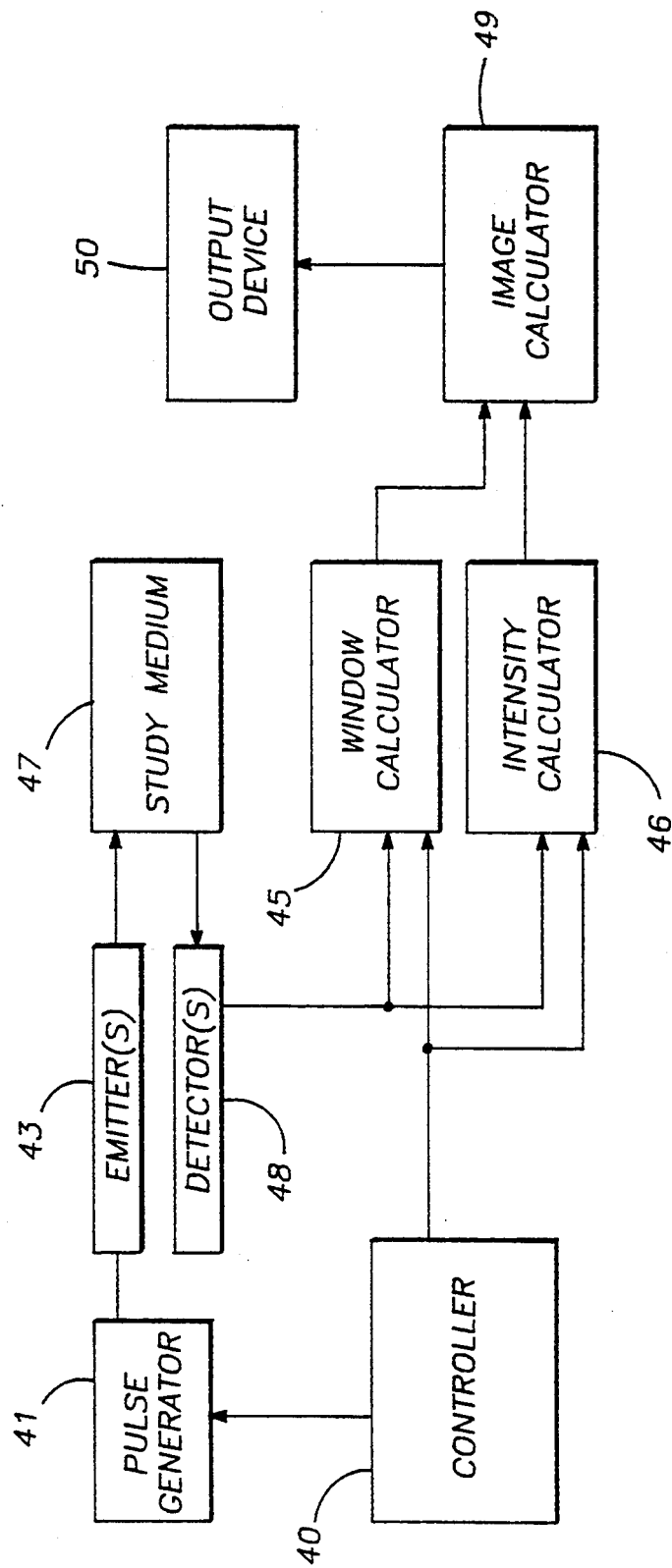
FIG. 3 is a block diagram of the major sections of the spectrophotometer.

In FIG. 3 the workings of the device are revealed in functional blocks. Here, controller 40 sends signals to pulse generator 41, in turn controlling light output from selected light sources in emitter 43. With each pulsed output, controller 40 also sends a timing pulse to window calculator 45 and intensity calculator 46 for use in processing detected signals. Signals returning from study medium 47 are picked up by detector unit 48 and sent to calculators 45 and 46. Window calculator 45 assesses the delay between emission of a light pulse by emitter 43 to allow only photons arriving during the defined window to be counted at intensity calculator 46. Output from calculators 45 and 46 are used by image calculator 49 to form an image, which is made available to the user on output device 50.

Methods of determining absorbance, derived from intensity, and path lengths, derived from window gating, are multiple, but fall within the scope of this invention if both coexist in one device for the purpose of calculating spatial distribution of light absorbing substances. In this embodiment, path lengths are estimated by constraining the time of flight of each photon with a window gate (termed time-constrained time-of-flight and absorbance, or tc-TOFA spectroscopy), but the effect can be achieved using an optical gate, among others.

TYPICAL WAVEFORMS DURING OPERATION OF THE DEVICE

The operation of the device can be illuminated more fully by studying typical waveforms encountered during data acquisition. These 'typical' waveforms were taken from actual data obtained using one embodiment of the device. These waveforms are provided as examples only, and no limitation of design or operation of the device by the specific patterns discussed below is implied or intended.

Of note, in the diagrams representing photon travel through the medium, photon movement is shown from left to right, and upward or downward deviation of the photons is representative of scattering. For graphs of photon intensity versus time, time is always shown on the x-axis and instantaneous intensity is shown on the y-axis, but neither axis is shown to scale as compression or expansion of each axis has been performed where needed for purpose of clarity.

Figure 4:
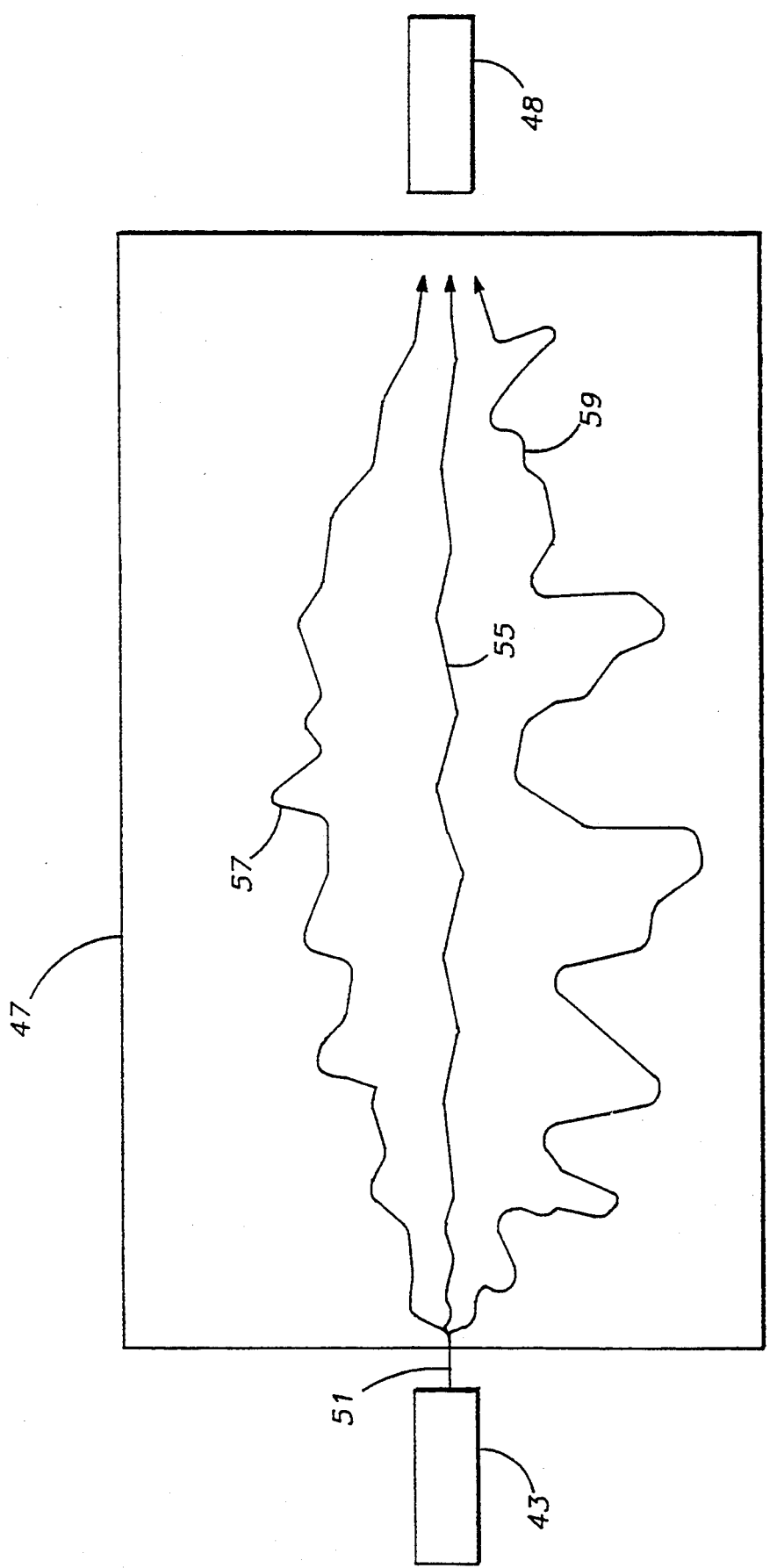
FIG. 4 illustrates the effect of scattering of light.

The effect of scattering upon a pulse of light is shown in FIG. 4. Here, emitter 43 emits a pulse of photons 51 into study medium 47. Scattering lengthens the distance traveled by photons between emitter 43 and detector 48, and thus delays arrival of the photons at the detector. Minimally scattering photons 55 travel the most direct line between emitter 43 and detector 48, and thus arrive first, while other photons scatter moderately 57 or greatly 59, and thus arrive later. Most of the initial pulse of photons 51 scatter moderately, and these photons arrive at detector 48 after the minimally scattering photons have arrived, but before the greatly scattering photons do so. Now that the effect of scattering is understood, the basis of the time constraint method can be demonstrated (FIGS. 5A–5F). Here, the top figures (FIGS. 5A, 5C, and 5E) are similar to FIG. 4, and show the passage of a group of photons through a study medium over time, while the lower figures (FIGS. 5B, 5D, and 5F) show the voltage at output 61 from detector 48 at the same instant in time as the figure above. In FIG. 5A, photon pulse 51, consisting of a group of photons all emitted from emitter 43 at about the same instant, has already traveled into medium 47. Minimally scattering photons 55 have passed entirely through the medium, and are arriving at detector 48. Moderately scattering photons 57 and greatly scattering photons 59 are all still traveling through the medium, as they have taken a longer route due to increased scattering. In FIG. 5B, output 61 of detector 48 is shown at the same time point as FIG. 5A. Output 61 is non-zero and rising, reflecting the arrival of minimally scattering photons 55 at detector 48. Moderately-scattering photons 57 and greatly-scattering photons 59 are still en route to the detector, and thus have not registered at this time.

In FIGS. 5A and 5B only minimally scattering photons have had enough time to reach detector 48, whereas in FIG. 5C more time has elapsed such that moderately scattering photons 57 are now arriving at detector 48. Greatly scattering photons 59 still have not yet reached detector 48. FIG. 5D shows that output 61 of detector 48 is now maximized. This is because the most of the photons from pulse 51 scatter moderately. In FIG. 5E, yet more time has passed, and greatly-scattering photons 59 are now finally arriving at detector 48. In FIG. 5F, the intensity reflects the greatly scattering photons.

Time-intensity curve 63 represents the intensity of light at detector 48 over time in the absence of any object placed between emitter and detector, and will be referred to as reference time-intensity curve 63. Different portions of reference curve 63 represent photons with different amounts of scattering. The left-most portion of the curve represents intensity of minimally scattering photons 65; the middle portion represents intensity of moderately scattering photons 67; the right-most region represents intensity of greatly scattering photons 69. Thus, the earliest detected photons in reference waveform 63 have traveled the least far, while the latest detected photons have traveled the furthest of all. In practice, there is no clear division between groups of photons with different amounts of scattering, but this continuous function has been simplified for the purpose of illustration into three groups (minimally scattering 65, moderately scattering 67, and greatly scattering 69) for the purpose of illustration. The shape of the time-intensity curve, a reflection of when photons arrive at detector 48, can be modified by material through which the light passes (FIGS. 6A–6F). In FIG. 6A, light-blocking solid rod 87 has been placed such that it blocks the direct path between source 43 and detector 48. Minimally scattering photons 55 are completely stopped by rod 87, while moderately scattering 57 and greatly scattering 59 photons pass unimpeded by traveling around the rod. In FIG. 6B, this shows up at then output of detector 48 as time-intensity curve 93, which is flattened in the early part as compared to reference wave 63. FIG. 6C, representing the same event as in FIG. 6A after additional time has passed, shows both moderately scattering photons 57 and greatly scattering photons 59 arriving normally at the detector, and thus the last half of time-intensity curve 91 is very similar to reference wave 63. When time-intensity curve 93 is studied in FIG. 6D, intensity of minimally scattering photons 65 is much less than in reference curve 63, while intensity of the moderately-scattering 67 and greatly scattering photons 69 are the same for both curves.

This result may be contrasted with FIG. 6E, in which two pairs of light-blocking rods, rods 103 and 105, are placed on either side of the direct path between source 43 and detector 48. Here, minimally scattering photons 55 are not blocked, whereas moderately scattering photons 57 and greatly scattering photons 59 are now completely blocked by the rods. FIG. 6F shows the effect of rods 103 and 105 on dual-blocked time-intensity curve 107, as compared to reference waveform 63. Intensity of minimally scattered photons 65 is the same for both reference and rod-blocked waveforms, whereas intensity of moderately scattering photons 67 and greatly scattering photons 69 is reduced in curve 107 compared to reference curve 63.

Figure 7:
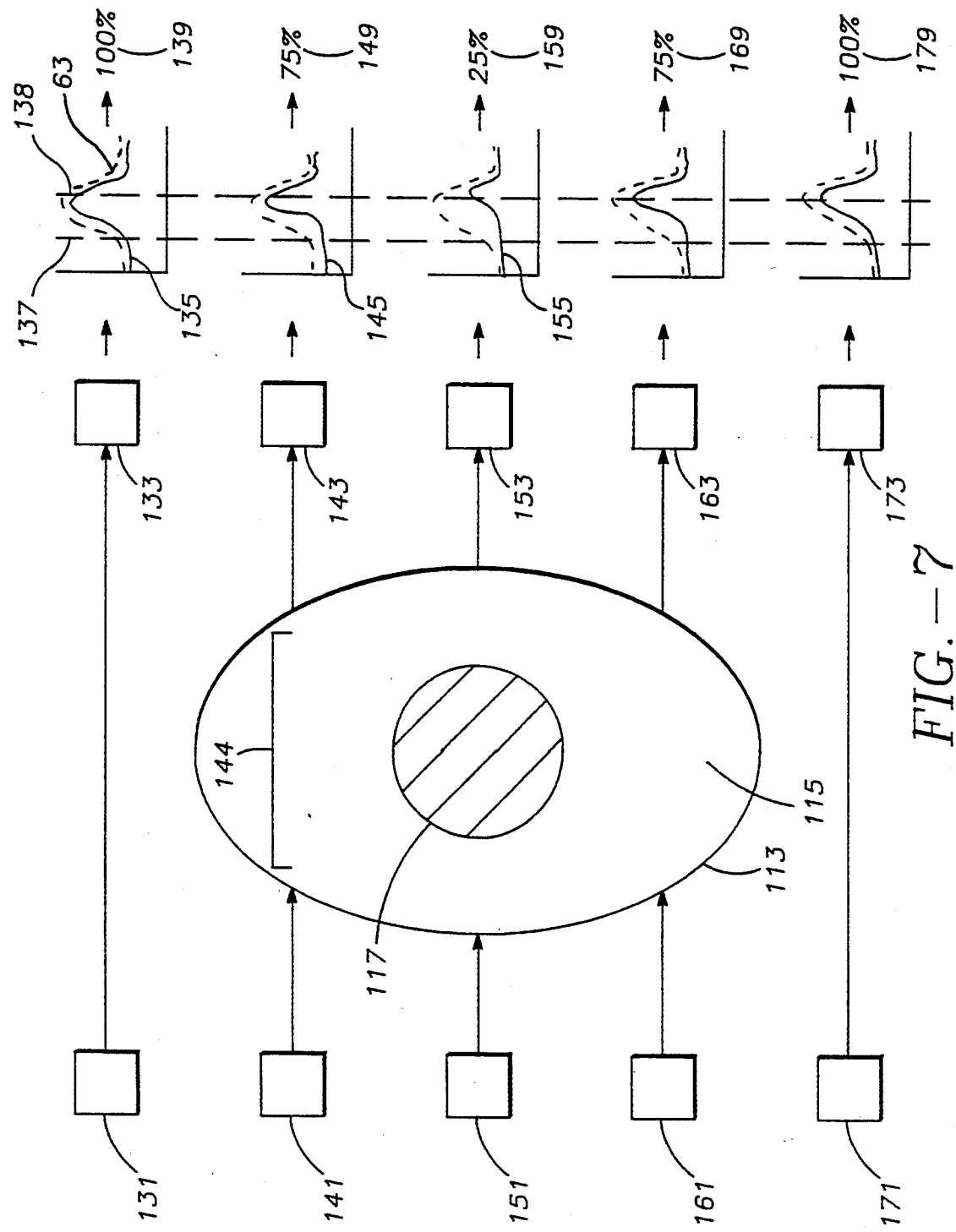
FIG. 7 illustrates the method of producing one type of image.

Multiple time-intensity curves may be obtained from a single object as a first step toward making an image. In FIG. 7, time-intensity curves are measured at five locations on object 113. Object 113 consists of mildly absorbent outside layer 115 surrounding highly scattering and absorbent core 117. In the first measurement in FIG. 7, emitter 43 is positioned at 131 and detector 48 is positioned at 133. The result is time-intensity curve 135, which is compared to reference curve 63 (shown as a dashed line). A narrow measurement window is defined as the interval between time marks 137 and 138. This narrow window restricts measurement in this example to the early portion of the time-intensity curve, the portion that represents intensity of minimally scattering photons 65. Taking a ratio of intensities of sample curve 135 and reference 63 within time marks 37 and 138 yields result 139, which in this case is 100%. This result indicates that sample curve 135 is 100% as bright as reference curve 63 over the narrow window specified by time-marks 137 and 138.

In the second measurement, emitter 43 is moved to position 141, and detector 48 is moved to position 143. Region 115 of object 113 now interrupts the direct travel between emitter 43 and detector 48, shown at 144. Comparison of sample curve 145 to reference curve 63 yields result 149, in this case 75%, indicating that minimally scattering photon intensity 65 has been reduced to 75% of reference intensity in region 115 of object 113. Similarly, placing emitter 43 at 151 and detector 48 at 153 yields sample time-intensity curve 155, and result 159, in this case 25%, indicating that minimally scattering photon intensity 65 has been reduced to 25% compared to reference in region 117 of object 113. A fourth scan at 161 and 163 yields result 169, while a final scan at 171 and 173 yields result 179.

Figures 8A, 8B:
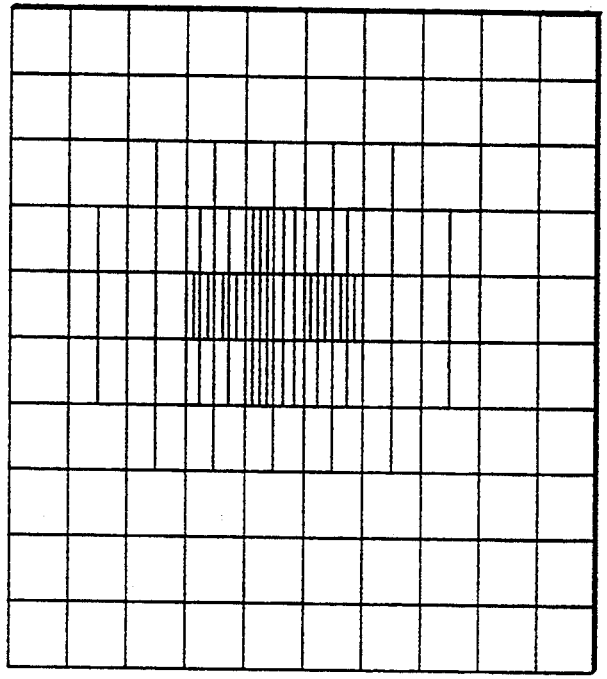
FIG. 8 shows a sample data table and image of an object.

Instead of measuring one row of locations, as was illustrated in FIG. 7, an object may be scanned in two or more dimensions. If object 113 is, for example, an olive, a two-dimensional scan could yield the data table shown in FIG. 8A. This data table would represent the percentage of minimally scattered photons measured during a narrow window and compared to a reference, and measured at multiple locations in two dimensions. Increasing the number of columns and rows measured improves resolution, while graphing the results, as shown in FIG. 8B, facilitates interpretation of the image.

This technique can easily be extended to three dimensions, to allow tomographic imaging. The resulting image can be related to the distribution of absorbance, concentration, scattering, or other features of the study medium. The relative number of photons arriving within a window can serve as the basis for the image, as can a complex function such as the timing of the window that first contains significant numbers of photons.

If all photons had been measured, rather than measuring only photons within a narrow time window, it would be difficult to identify through what region of object 113 photons had passed. Limiting the time window to measure only the minimally scattering photons insures that only photons that have passed through a region directly between an emitter and a detector are measured. For some types of images, however, combinations of regions may be used in the result calculation. In addition, the scan can use different patterns of measurement (e.g., moving detector and emitter in a circle as opposed to a line), to allow tomographic imaging. Next, emitter and detector do not need to be on opposite sides of a subject. Furthermore, use of an optical shutter, to divide light into time-constrained components falls within the spirit of this invention.

Figure 9:
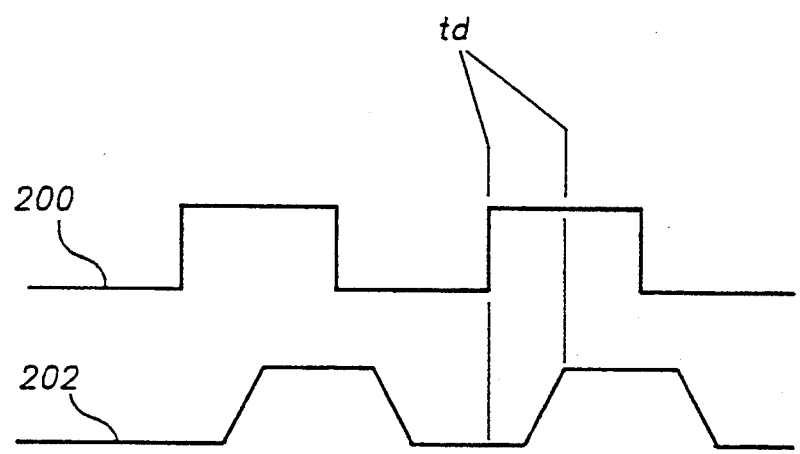
FIG. 9 shows a waveform representative of a modulated optical signal applied to a sample, and also shows the waveform after being phase-shifted subsequent to propagation through the sample.

Modification of the measurement to introduce other methods of time-constraining the signal, such as interferometry or phase-shift spectroscopy, all fall within the spirit of the device, if used in a combination to measure or select intensity measurements indicative of path of travel. For example, in phase shift spectroscopy the delay in phase of a modulated signal transmitted through a sample is converted into an estimate of path length. Specifically, FIG. 9 shows a waveform 200 representative of a modulated signal applied to a sample, while waveform 202 corresponds to the modulated signal after propagation through the sample. The duration of the phase delay $t_d$ is proportional to the average path length traversed by the modulated signal during propagation through the sample. Specifically, path length L may be determined in accordance with the following expression, $$L = t_d c/n$$

where c is the speed of light and n is the refractive index of the sample. The value of $t_d$ may be determined by coupling the emitter and intensity detector to a conventional phase detector operative to determine the phase differential between the waveforms 200 and 202.

The device as described is capable of measuring the spatial distribution of light absorbing or other radiation absorbing substances contained in a radiation scattering media. The technology cited in this embodiment is currently available to construct this device inexpensively, to make the device portable, and to have it operate in real time. Furthermore, construction and methods of this device are unique, distinct from other spectrophotometers in the art. Multiple, significant advantages of this design are inherent from an incorporation of both time of flight and absorbance measurements.

The following examples of measurements performed using the inventive spectrophotometer are included so as to enhance understanding of the foregoing description of the device. As is illustrated by the following examples, scattering media such as the human body may be characterized by quantitation, by localization (or imaging), or by a combination of quantitation and imaging.

EXAMPLE #1

Imaging in One or More Dimensions Using Time-of-Flight/Absorbance

As noted above, it is believed that previous methods of measuring absorbance have not been path-corrected. That is, conventional absorbance-measuring techniques have generally not taken into account the various paths traveled by photons penetrating a scattering object. In contrast, in an embodiment of the present invention depicted in FIG. 10 a constant fraction of the early-arriving photons passing substantially directly through a scattering object are detected. This approach has resulted in simplified calculation and successful imaging of attenuating material placed in light-scattering media. As employed herein, the term attenuating material is intended to encompass absorptive substances and the like tending to decrease the measured intensity of photons passing through the scattering object.

Figure 10:
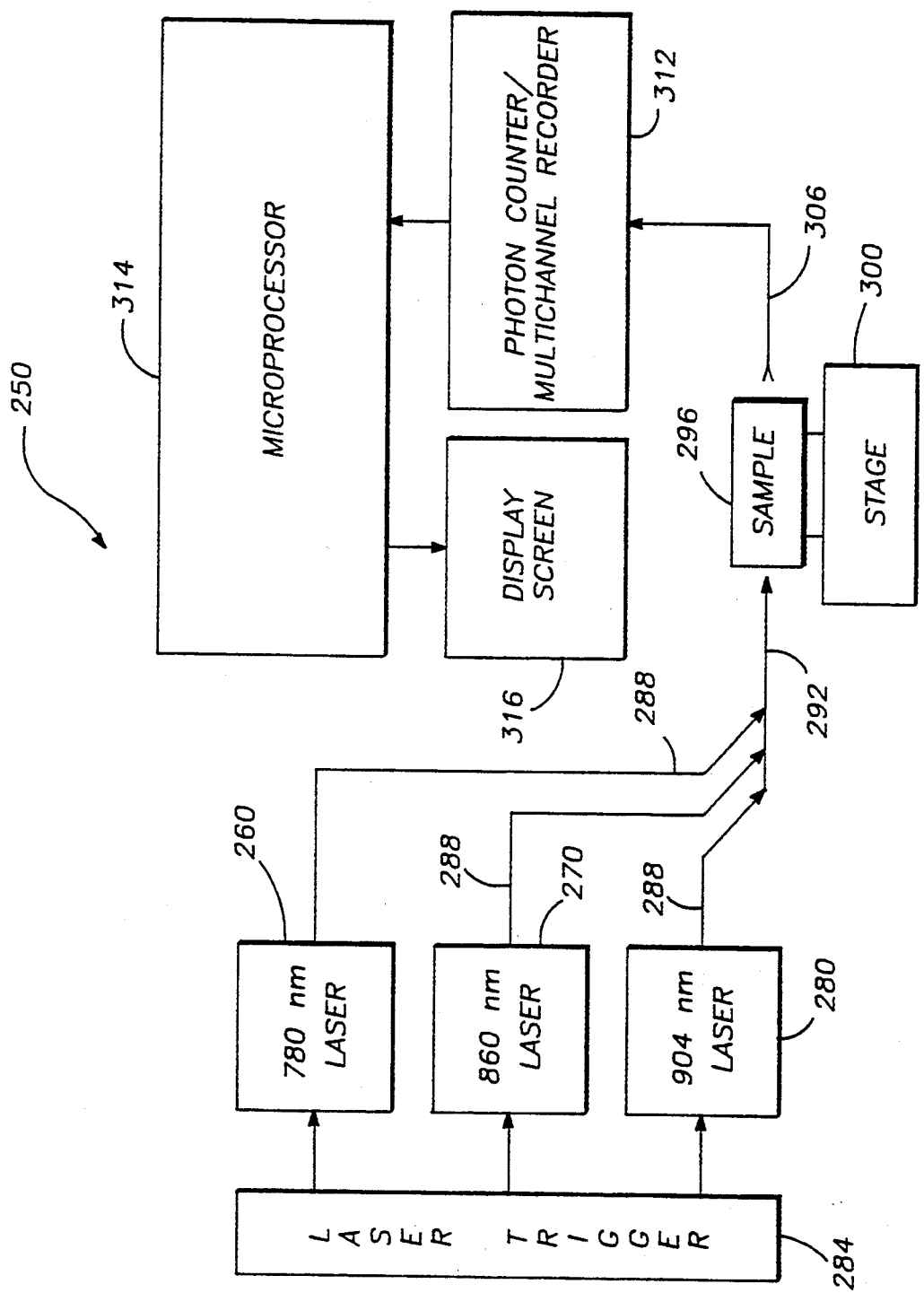
FIG. 10 is a block diagrammatic representation of a time-of-flight and absorbance (TOFA) system operative to produce an image of a sample in accordance with the invention.

Referring to FIG. 10, there is shown a block diagrammatic representation of a time-of-flight and absorbance (TOFA) system 250 operative to produce an image of a sample in accordance with the present invention. The system 250 includes first, second and third diode lasers 260, 270 and 280 controlled by laser trigger 284. The lasers 260, 270 and 280 respectively operate at wavelengths of 785 nm, 850 nm, and 904 nm, and are coupled by fiber optics 288 to a fiber optic emitter 292 positioned to illuminate a sample 296. The sample 296 will generally comprise a tissue sample or the like having one or more attenuating constituents surrounded by a scattering medium, e.g., blood or a lipid solution. The sample 296 rests on X-Y translational stage 300, wherein the X-Y coordinate plane associated with the stage 300 is normal to the plane of FIG. 10. As is described in further detail below, images are generated during a two-dimensional scan by accumulating a time-of-flight/absorbance (TOFA) curve at each (X,Y) stage location based on characteristics of the sample 296 directly between the emitter fiber 292 and a detector fiber 306 at that stage location.

In the embodiment of FIG. 10 the illumination provided by the emitter 292 is in the form of a pulsed beam having a diameter on the order of 50 μm and a pulse width of approximately 100 ps. The peak power of the pulsed beam will generally range from 10 mW at 785 nm to 50 mW at 904 nm, and will have a repetition rate of 33 kHz. Triggering of the lasers 260, 270 and 280 by the laser trigger 284 is reproducible to within approximately 2 ps. Although the trigger 284 operates to fire the lasers 260, 270 and 280 simultaneously, the signals produced by each are temporally separated by varying the length of the fiber optics 288 respectively connected to each. The detector fiber 306, 50 μm in diameter and positioned such that linear photon collection is maximized, collimates and transmits detected light to a solid-state photon counter/multi-channel recorder 312 with up to 25% efficiency. Photon counter 312 is controlled by microprocessor 314, which is also operative to drive display screen 316.

Figure 11B:
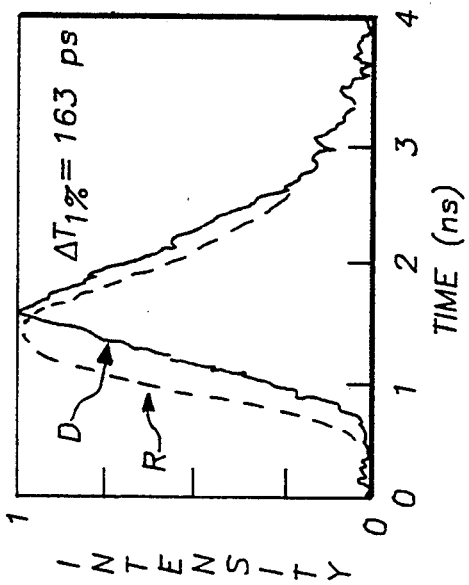
FIGS. 11B–11D illustrate the manner in which the presence of attenuating constituents in various regions of the sample scattering medium affects time variation in the quantity of light passing therethrough.
Figure 11D:
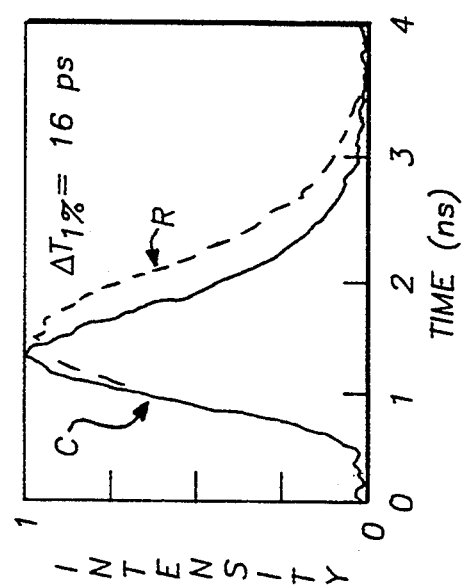
Figure 11A:
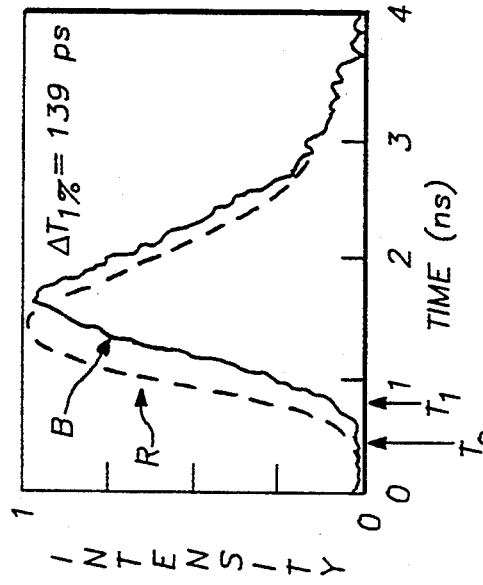
FIG. 11A is a graph of a reference curve R representative of light detected as a function of time through a sample scattering medium in the absence of any attenuating constituents therein.

Referring to FIG. 11A, the manner in which the system 250 operates to create a separate reference TOFA curve R characterizing transmission of the pulses from each of the lasers 260, 270 and 280 through the scattering medium of sample 296 will now be described. The reference curve R is a graph depicting intensity of light detected by solid-state photon counter 312 as a function of time through the scattering medium of sample 296 in the absence of any attenuating constituents therein. Time zero of FIG. 11A corresponds to the time required for light emitted by emitter fiber 292 to reach detector fiber 306 through a non-scattering medium (e.g., water). As a first step in generating the curve R the sample 296 is placed on stage 300 prior to the introduction into sample 296 of any attenuating constituents. Each of the lasers 260, 270, 280 are then triggered to emit numerous (e.g., 256) pulses in sequence, with the detector fiber 306 being sampled by photon counter 312 after a slightly longer delay interval subsequent to the emission of each pulse. In this way the light intensity within the detector fiber 306 is sampled by photon counter/multichannel recorder 312, once for each pulse, over a series of sequential, partially overlapping detection windows. The intensity samples are stored within the photon counter/multichannel recorder 312 so as to provide a reference intensity curve R for each of the lasers 260, 270, 280. Since the time interval between adjacent sampling windows may be selected to be as brief as approximately 2 picoseconds, multiple curves may be accumulated and averaged in generating the curve R associated with a given laser wavelength.

After a reference curve has been generated for each laser wavelength through each pixel region of the sample 296, the attenuating constituents which it is desired to image are placed within the sample 296. The same procedure described above used in generating the reference curves R is then employed to synthesize the sample intensity curves B, C and D respectively shown in FIGS. 11B, 11C and 11D. In accordance with the invention a separate sample intensity curve is generated for each cell in a grid of individual pixel regions, i.e., X-Y locations, of sample 296. This is effected by programming microprocessor 314 to maneuver stage 300 in a desired X-Y scan pattern, which in a preferred embodiment comprises translation in 500 μm steps over each axis.

In the specific example shown in FIG. 11A the reference curve R was produced by using laser 260 (785 nm) to illuminate a single pixel region of a 700 cm³ cube, similar in volume to the head of a neonate, filled with 0.2% intralipid to produce scattering similar in magnitude to neonatal brain. In FIG. 11B the curve B was produced after placing a light-blocking black matte rod within the lipid directly in the center of the pixel region. The sample intensity curve C was generated by positioning black matte rods within the lipid on either side of the emitter-detector axis, i.e., on the axial line extending between the emitter and detector fibers 292 and 306. Similarly, in FIG. 11D human tissue was placed directly on the emitter-detector axis within the pixel region. In FIGS. 11A–11D the separation of the emitter 292 and detector 306 was 90 mm, the detection window width was 5 ns, and the wavelength used was 785 nm.

As was previously explained, the intensity of various portions of reference curve R represent photons having undergone differing amounts of scattering. The leftmost portion of the curve R represents intensity of photons least scattered by the scattering medium, the middle portion represents intensity of moderately scattering photons, and the right-most region represents the intensity of widely-scattered photons. In accordance with the invention, the value of an image pixel associated with each pixel region is determined by comparing the shape of the curve R with the sample intensity curve from the corresponding pixel region. This comparison may be effected in part by, for example, determining the different times required for 1% of the total light intensity to arrive at the detector 306 (1% threshold time) when the attenuating and scattering constituents are respectively absent from, and present within, the sample 296. Referring to FIGS. 11A and 11B, direct blockage of the optical path between the emitter 292 and detector 306 results in an increase in the 1% threshold time from $T_o$ to $T_1$, i.e., $\Delta T1\% = 139$ picoseconds. A similar 1% threshold delay is observed in FIG. 11D which, again, corresponds to a sample having human tissue along the emitter-detector axis.

Figure 11C:
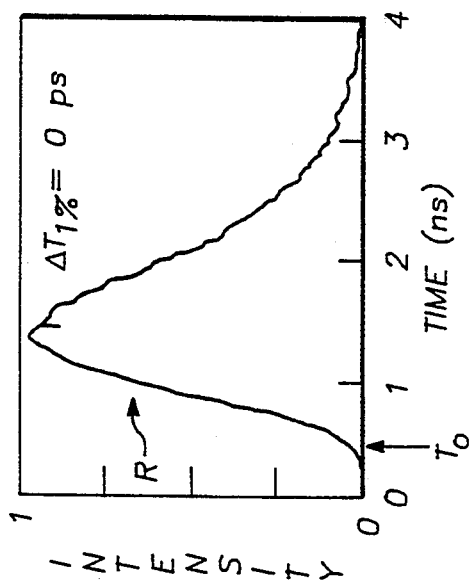

In contrast, blocking the peripheral optical path as in FIG. 11C results in fewer later-arriving photons but does not appreciably alter the 1% threshold time. The value of $\Delta T1\%$ thus provides a relatively precise measure of the extent to which light propagating close to the emitter-detector path is obscured by attenuating constituents within the sample 296. Hence, an image of the sample 296 may be created by determining the value of $\Delta T1\%$ associated with the time-intensity curves (FIGS. 11B–11D) for each of the X-Y pixel locations of the image. The 1% threshold times will typically be computed by microprocessor 314 based on the information accumulated by multi-channel recorder 312, and will then be displayed in the form of an image on display screen 316.

Time-intensity curves such as those shown in FIGS. 11A–11D may also be used in deriving an image of the sample 296 based on concentration of the attenuating constituents proximate the emitter-detector axis of each pixel region. Referring to equation (2), computation of concentration requires determination of the absorbance A and path length L of each pixel region. An estimate of absorbance is made by comparing the area under the time-intensity curve associated with a particular pixel region of the sample 296 with the area under a time-intensity curve (not shown) compiled with a non-scattering medium between the emitter 292 and detector 306. Specifically, the absorbance A is given by, $$A = \log_{10}(I_{NS}/I_S)$$

where $I_{NS}$ refers to the measured intensity through the non-scattering medium and $I_S$ denotes the measured intensity through the pixel region of interest.

Concentration may then be computed after determining mean path length L by, for example, (a) using the time-intensity curve associated with a pixel region to obtain an average of the times-of-flight of the photons propagating therethrough, and (b) multiplying the average time-of-flight by the velocity of radiation through the sample 296.

Referring to FIG. 11A, through lipid alone the mean path length L was found to be 362 mm and photon attenuation exceeded $1:10^5$ relative to transmission through water alone. A ratio of scattered to unscattered mean path length was 4.09, which is believed to be similar to the lengthening produced by scattering in neonatal brain tissue.

The example depicted in FIGS. 11A–11D indicates that path-resolved imaging in accordance with the present invention allows for the discrimination between samples having differing distributions of attenuating constituents. In contrast, conventional devices disposed to measure absorbance alone are not capable of making such discriminations.

The time-intensity information accumulated by the multi-channel recorder 312 may be used in a variety of ways to generate an image of the sample 296. For example, the image pixel corresponding to each X-Y stage location could be assigned a false color, using a log magnitude scale, based on the average photon intensity of the region. The resulting X-Y matrix of false colors could then be used to create a color image on film. Similarly, the change in threshold delay relative to a sample not including any attenuating constituents could also be used as a basis for assigning a false color to a given pixel region.

The imaging method described with reference to FIGS. 11A–11D may easily be extended to three-dimensions by performing scans along image planes orthogonal to a plurality of axes intersecting the sample 296. For example, scans could be performed over image planes orthogonal to the X, Y, and Z axes as well as over a plane orthogonal to each of these axes by forty-five degrees. In one embodiment a three-dimensional image synthesis routine is performed upon a three-dimensional matrix of the 1% threshold delays accumulated during the scanning of each plane. The value stored within each cell of this three-dimensional matrix was determined by computing the product of the threshold delays from the X-Y locations of each of the four planar images having emitter-detector axes linearly aligned with the corresponding cell of the three-dimensional matrix. A false color was assigned to each element within the three-dimensional matrix so as to enable the image to be recorded on film.

An example has also been performed which is designed to demonstrate the effect of time-resolved measurements upon standard quantitative approaches, such as pulse oximetry, and in new approaches, such as arterial/venous differentiation of oxygenation. As is described below, the combination of path and absorbance measurements contemplated by the present invention allows a novel and more accurate method for determination of quantitative measurements in blood and tissue. In one embodiment the present invention may be used to provide an image of concentration of N attenuating constituents within a scattering medium by solving the following set of equations for the concentrations $C_1$ through $C_N$:

$$A_1 = \epsilon_1 C_1 L_1$$
$$A_1 = \epsilon_2 C_2 L_2$$
$$\vdots$$
$$A_N = \epsilon_N C_N L_N,$$

where numbered subscripts refer to attenuating constituents 1 through N present within the scattering medium. The scattering medium is illuminated with N wavelengths of radiation $\lambda_1$ through $\lambda_N$, with $A_n$ and $L_n$ being measured during illumination at each wavelength $\lambda_n$. The values of $A_n$ and $L_n$ are stored for each wavelength, and the values of $C_1$ through $C_N$ may be obtained by using a digital computer or the like to solve the above N simultaneous equations.

EXAMPLE #2

Quantitation Measurement of Venous Blood Oxygenation

In this example, data were collected from a human subject using a time-of-flight/absorbance (TOFA) scanner operative in accordance with the methodology described with reference to FIG. 10. The TOFA scanner was strapped to the foot of the subject, and measurements were performed with the foot in both lowered and raised positions. It should be appreciated that the volume of blood in the veins (venous blood) changes with positional movement of the extremity, while there are no appreciable corresponding changes in arterial concentration. Hence, changes in absorbance are due primarily only to changes in the column of venous blood present in the limb. The foot was initially placed high above the waist, and absorbance and path were measured at two different wavelengths (785 and 850 nm). Absorbance and path were again measured after the foot had been lowered to the ground, and the following data was collected:

| Data for 785 nm: | Raised (start) | Lowered (end) | Change |
|---|---|---|---|
| ABSORBANCE | 6.408 | 7.678 | 1.270 |
| PATH LENGTH | 119 mm | 93 mm | 36 mm |
| Data for 850 nm: | Raised | Lowered | Change |
| ABSORBANCE | 6.770 | 7.986 | 1.216 |
| PATH LENGTH | 87 mm | 61 mm | 26 mm |

The fact that blood contains hemoglobin, a protein which carries oxygen, may be exploited in measuring the oxygenation of venous blood. This protein is found in two forms: oxygenated hemoglobin (abbreviated $HbO_2$) and hemoglobin without oxygen (abbreviated Hb). When combining hemoglobin with oxygen, an equation can be written as:

$$Hb + O_2 \rightleftharpoons HbO_2.$$

In certain medical applications the percentage of blood containing oxygen is of particular significance. For arterial blood this parameter is termed the $S_aO_2$, while for venous blood it is termed the $S_vO_2$. An equation describing percent oxygenation in venous blood is:

$$S_vO_2\% = \frac{[HbO_2] \times 100}{[HbO_2] + [Hb]}.$$

One can solve for this equation by monitoring changes in absorbance, since the cumulative change in absorbance is proportional to the changes in the absorbance of each component. Selecting wavelengths of light that minimize absorption of light by substances other than hemoglobins yields a Beer's Law equation of:

$$A = \epsilon HbCHbL + \epsilon HbO_2CHbO_2L + K,$$

where K is a constant absorbance unaffected by the illuminating light. Hence, changes in absorbance are expressed by:

$$\Delta A = A_{start} - A_{end}$$

$$= (\epsilon Hb[HB]endL\\ end + \epsilon HbO2[HbO2]endLend) - \epsilon Hb[Hb]startLstart + \epsilon HbO2[HbO_2]startLstart).$$

Epsilon ($\epsilon$) is a known constant, and has a different value for each substance at each wavelength. For example, in one reference the values of epsilon are given by:

| Values for $\epsilon$ | Hb | HbO2 |
|---|---|---|
| 785 nm | 0.32 | 0.17 |
| 850 nm | 0.22 | 0.26 |

These values for epsilon may be substituted into the foregoing to yield two delta-A ($\Delta A$) equations, one for each wavelength, as:

$$\Delta A785 = (0.32[Hb]endLend + 0.17[HbO2]endLend) - 0.32[Hbstart]Lstart + 0.17[HbO_2]startLstart).$$

$$\Delta A850 = (0.22[Hb]endLend + 0.26[HbO2]endLend) - 0.22[Hbstart]Lstart + 0.26[HbO_2]startLstart).$$

Similar measurements could be accomplished by monitoring phase shift of the illuminating pulses in order to determine time of flight through the sample. In certain applications it may also be desired to sum absorbance over the entire time-intensity curve, rather than using only mean absorbance and mean path values, such that the width and distribution of the time-intensity curve is used to solve quantitation equations more accurately.

EXAMPLE #3

Combination of Quantitation and Localization in Whole-Body Pulse-Oximetry

This example illustrates that the two methods of time-resolved spectroscopy (quantitation and imaging) may be combined in order to effect localized spectroscopy. This represents a significant advance over conventional pulse oximetry, which generally may not be employed to carry out localized measurements. Localized spectroscopy could be of particular utility in, for example, medical applications requiring monitoring of the distribution of oxygenation.

Time-resolved spectroscopy could allow focal measurements of arterial saturation and construction of an image of saturation. This could be of use, for example, in infants with certain types of problems (such as one type called "PDA") in which the amount of oxygen is different in different arteries. Another example would be in the imaging of heart problems. Time-resolution should allow localization of the measurement, while measurement of venous blood saturation should allow estimates of the sufficiency of oxygen delivery to that tissue. Such a measurement could allow noninvasive localization of heart attacks, for example.

In accordance with this technique a sample is scanned over an X-Y grid of locations in the manner described above. In this case, however, the value determined for each image pixel is not threshold time, but rather corresponds to the arterial or venous oxygen saturation. These saturation values are computed as described in the quantitation examples above using measurements of two or more wavelengths. Each arterial saturation measurement is then placed into the cell of a memory matrix associated with a corresponding X-Y measurement location. Assigning a false-color value to each entry within this matrix would allow an image of oxygenation to be collected and displayed.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. A spectrophotometer for providing an image of a radiation scattering medium having one or more radiation attenuating constituents, comprising:
   light source means for illuminating said medium from a source location at a time $t_0$ with electromagnetic radiation of at least one wavelength, said electromagnetic radiation propagating through said medium over a plurality of paths;
   means for detecting, during a set of detection windows commencing at selected times relative to time $t_0$, portions of said electromagnetic radiation emerging from said medium at a first detection location after having propagated through said medium from said source location to said first detection location over a corresponding set of paths of selected length;
   intensity measuring means for measuring intensity of each of said detected portions of electromagnetic radiation during said detection windows wherein said measured intensities are a function of attenuation of said region; and
   means for generating said image based upon said intensities measured during each of said detection windows and upon corresponding ones of said paths of selected length.

2. The spectrophotometer of claim 1 wherein said means for detecting includes an array of detectors for detecting, at a first plurality of locations proximate said medium, said electromagnetic radiation having propagated through said plurality of paths through said medium.

3. The spectrophotometer of claim 2 wherein said plurality of locations includes a two-dimensional array of locations, and wherein said means for generating an image includes means for generating a two-dimensional image based on said measured intensities of radiation detected by said array of detectors.

4. The spectrophotometer of claim 1 wherein said means for detecting includes a scanning detector for detecting, at a first plurality of locations proximate said medium, said electromagnetic radiation having propagated through said plurality of of paths through said medium.

5. The spectrophotometer of claims 2 or 4 wherein said light source means includes means for illuminating said medium from a second plurality of locations proximate said medium.

6. The spectrophotometer of claim 1 wherein said intensity measuring means includes means for comparing said intensities measured during each of said detection windows with a reference intensity corresponding to measured intensity of radiation propagating through said medium along a reference path.

7. The spectrophotometer of claim 1 wherein said light source means includes a laser for emitting a pulse of electromagnetic radiation, and wherein said detecting means includes a time-gated detector actuated during a predefined detection interval subsequent to said emission of said pulse.

8. The spectrophotometer of claim 1 wherein said light source means includes laser means for generating electromagnetic radiation at a plurality of selectable wavelengths.

9. The spectrophotometer of claim 1 wherein said means for detecting includes a time-gated detector for producing detection signals only during multiple predefined detection intervals in response to said electromagnetic radiation incident thereon.

10. The spectrophotometer of claim 1 further including means for computing concentration, C, of one or more of said radiation attenuating constituents in accordance with the expression, $$C = A/\epsilon L$$

wherein A is derived from a function of said measured intensities of said electromagnetic radiation, $\epsilon$ is a known constant, and L corresponds to a function of said path lengths.

11. The spectrophotometer of claim 1 wherein said means for generating said image includes means for generating an image representing concentration of said one or more radiation attenuating constituents.

12. The spectrophotometer of claim 1 wherein said detecting means includes means for detecting portions of said electromagnetic radiation having traversed nonlinear paths during propagation through said medium, said nonlinear paths being of substantially different path length than a linear transmission path through said medium.

13. The spectrophotometer of claim 1 wherein said means for generating said image includes means for formulating a time-intensity relationship in accordance with said intensities measured during each of said detection windows, and deriving an image parameter using said time-intensity relationship and said paths of selected length.

14. A spectrophotometer for providing an image of a radiation scattering medium having one or more radiation attenuating constituents, comprising:
 means for illuminating said medium with electromagnetic radiation of at least one wavelength, and for modulating intensity of said electromagnetic energy in accordance with a phase-modulation waveform;
 means for detecting portions of said electromagnetic radiation propagating through a region of said medium;
 means for determining a phase shift Of said phase-modulation waveform associated with each of said detected portions of said electromagnetic radiation, each of said phase shifts corresponding to a function of the distribution of radiation path lengths through said region of said medium;
 means for measuring intensity of each of said detected portions of electromagnetic radiation wherein each of said measured intensities corresponds to attenuation of said region; and
 means for generating said image in accordance with said measured intensities and phase shifts.

15. The spectrophotometer of claim 14 wherein said means for illuminating includes means for generating an illumination beam and a reference beam.

16. The spectrophotometer of claim 15 wherein said means for determining phase shift includes means for comparing said reference beam with portions of said illumination beam incident upon said means for detecting.

17. The spectrophotometer of claim 14 wherein said means for detecting includes an array of detectors for detecting, at a first plurality of locations proximate said medium, said electromagnetic radiation having propagated through a plurality of regions of said medium.

18. The spectrophotometer of claim 14 wherein said means for detecting includes a scanning detector for detecting, at a first plurality of locations proximate said medium, said electromagnetic radiation having propagated through a plurality of regions of said medium.

19. The spectrophotometer of claims 17 or 18 wherein said means for illuminating includes light source means for illuminating said medium at a second plurality of locations proximate said medium.

20. The spectrophotometer of claim 14 wherein said means for illuminating includes laser means for generating said electromagnetic radiation at a plurality of selectable wavelengths.

21. A method for providing an image of a radiation scattering medium having one or more radiation attenuating constituents, comprising the steps of:
 illuminating said medium with electromagnetic radiation of at least one wavelength from a source location at a time $t_0$, said electromagnetic radiation propagating through a region of said medium over a plurality of paths;
 detecting, during a set of detection windows commencing at selected times relative to time $t_0$, portions of said electromagnetic radiation emerging from said medium at a first detection location after having propagated through said medium from said source location to said first detection location over a corresponding set of paths of selected length;
 measuring intensity of each of said detected portions of electromagnetic radiation wherein said measured intensities are a function of attenuation of said region; and
 generating said image based upon said intensities measured during each of said detection windows at said first detection location and upon corresponding ones of said paths of selected length.

22. The method of claim 21 further including the step of detecting, at a first plurality of locations proximate said medium, said electromagnetic radiation having propagated over said plurality of paths through said medium.

23. The method of claim 22 further including the step of illuminating said medium from a second plurality of locations proximate said medium.

24. The method of claim 22 wherein said first plurality of locations includes a two-dimensional array of locations, and wherein said step of generating said image includes the step of generating a two-dimensional image based on measured intensities of radiation detected by said array of detectors.

25. The method of claim 21 wherein said step of measuring intensity includes the step of comparing said intensities measured during each of said detection windows with a reference intensity corresponding to measured intensity of radiation propagating through said medium along a reference path.

26. The method of claim 21 wherein said step of illuminating further includes the step of emitting a pulse of electromagnetic radiation, and wherein said step of detecting is performed during a predefined detection interval selected to begin at a predefined time subsequent to said emission of said pulse:

thereby resulting in detection of said electromagnetic radiation having traversed one of said paths of selected length.

27. The method of claim 21 wherein said step of illuminating includes the step of generating said electromagnetic radiation at a plurality of selectable wavelengths.

28. The method of claim 21 further including the step of computing concentration, C, of one or more of said radiation attenuating constituents in accordance with the expression, $$C = A/\epsilon L$$

wherein A is is derived from a function of said measured intensities of said electromagnetic radiation, $\epsilon$ is a known constant, and L corresponds to a function of said path lengths.

29. The method of claim 21 wherein said step of generating said image includes the step of generating an image representing concentration of said one or more radiation attenuating constituents.

30. The method of claim 21 wherein said step of detecting includes the step of detecting electromagnetic energy having traversed one or more nonlinear paths during propagation through said medium, said one or more nonlinear paths being of substantially different path length than a linear transmission path through said medium.

31. The method of claim 21 wherein said step of generating said image includes the step of formulating a time-intensity relationship in accordance with said intensities measured during each of said detection windows, and the step of deriving an image parameter using said time-intensity relationship and said paths of selected length.

32. A method for providing an image of a radiation scattering medium having one or more radiation attenuating constituents, comprising the steps of:

illuminating said medium with electromagnetic radiation of at least one wavelength, and modulating intensity of said electromagnetic energy in accordance with a phase-modulation waveform;

detecting portions of said electromagnetic radiation propagating through a region of said medium;

determining a phase shift of said phase-modulation waveform associated with each of said detected portions of said electromagnetic radiation, each of said phase shifts corresponding to a function of the distribution of radiation path lengths through said region of said medium;

measuring intensity of each of said detected portions of electromagnetic radiation wherein each of said measured intensities corresponds to attenuation of said region; and generating said image in accordance with said measured intensities and phase shifts.

33. The method of claim 32 wherein said step of illuminating includes the step of generating an illumination beam and a reference beam.

34. The method of claim 33 wherein said step of determining phase shift includes the step of comparing said reference beam with portions of said illumination beam.

35. The method of claim 34 further including the step of detecting, at a first plurality of locations proximate said medium, said electromagnetic radiation having propagated through a plurality of regions of said medium.

36. The method of claim 35 further including the step of illuminating said medium at a second plurality of locations proximate said medium.

37. The method of claim 32 wherein said step of illuminating includes the step of generating electromagnetic radiation at a plurality of selectable wavelengths.

38. A spectrophotometer for providing an image of a radiation scattering medium having one or more radiation attenuating constituents, comprising:

light source means for illuminating said medium with electromagnetic radiation characterized by a first time-intensity relationship, said electromagnetic radiation propagating through said medium over a plurality of paths:

detection means for detecting said electromagnetic radiation having propagated through said medium over at least one path of one or more selected lengths, said detection means including means for identifying a second-time intensity relationship characterizing said detected electromagnetic energy having propagated over said at least one path of said one or more selected lengths; and means for generating an image based on said one or more selected lengths and said second time-intensity relationship.

* * * * *